(12) United States Patent
Ysebaert

(10) Patent No.: US 6,248,114 B1
(45) Date of Patent: Jun. 19, 2001

(54) METHOD FOR FORMING SKIN GRAFTS

(75) Inventor: Willem Marie Ysebaert, Hendriklaan (NL)

(73) Assignee: Burncare B. V. (NL)

( * ) Notice: Subject to any disclaimer, the term of this patent is extended or adjusted under 35 U.S.C. 154(b) by 0 days.

(21) Appl. No.: 09/284,630

(22) PCT Filed: Oct. 14, 1997

(86) PCT No.: PCT/NL97/00573

§ 371 Date: Jul. 22, 1999

§ 102(e) Date: Jul. 22, 1999

(87) PCT Pub. No.: WO98/16158

PCT Pub. Date: Apr. 23, 1998

(30) Foreign Application Priority Data

Oct. 15, 1996 (NL) .................................................... 1004276

(51) Int. Cl.[7] ...................................................... A61B 17/50
(52) U.S. Cl. .............................................................. 606/132
(58) Field of Search ............................................... 606/132

(56) References Cited

U.S. PATENT DOCUMENTS 4,773,418 * 9/1988 Hettich ................................. 606/132
4,927,410 * 5/1990 Kovacs ................................... 600/36

* cited by examiner

*Primary Examiner*—Jeffrey A. Smith
*Assistant Examiner*—Eduardo C. Robert

(57) ABSTRACT

A method for forming skin grafts by cutting skin present on a porous carrier, using a cutting device. The carrier has a first side on which skin can be placed and a second side remote from the skin an present in a holder. The skin is placed on a first side of the porous carrier wherein a sub-atmospheric pressure is generated in the holder, on to the second side of the carrier remote from the skin, after which the skin is cut into skin grafts by the cutting device.

14 Claims, 9 Drawing Sheets

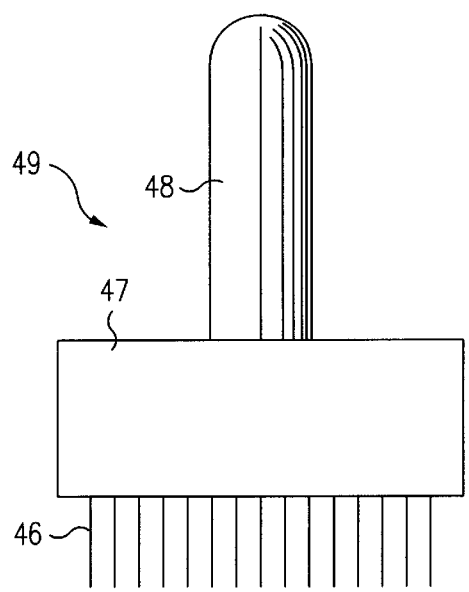
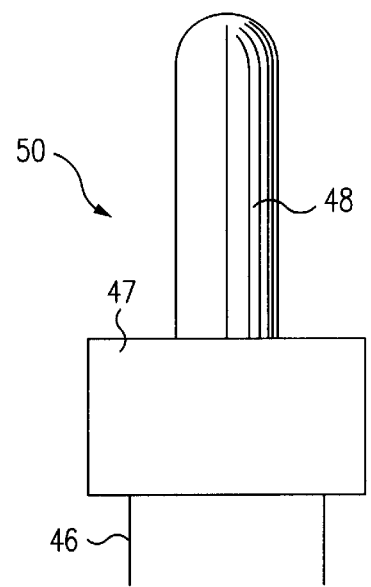
FIG. 8a
FIG. 9a
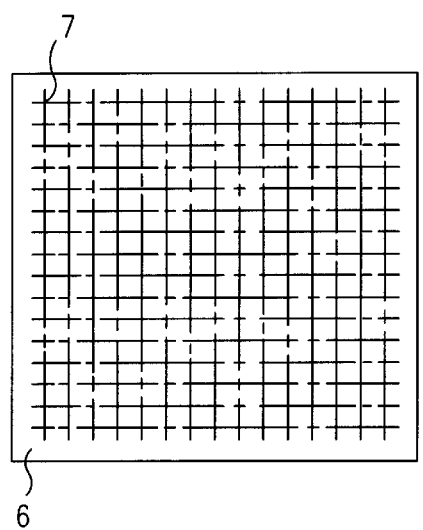
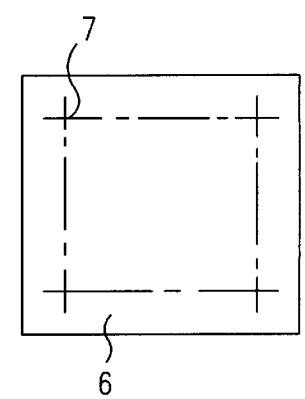
FIG. 8b
FIG. 9b

METHOD FOR FORMING SKIN GRAFTS

FIELD OF THE INVENTION

The present invention relates to a method for forming skin grafts by cutting skin present an a carrier, which carrier is present in a holder, using cutting means, and furthermore to such a holder to be used in forming skin grafts, a carrier, a contra carrier, a cutting table, clamping means and ejecting means to be used therewith. The present invention furthermore relates to a method for applying skin grafts to a burn.

BACKGROUND

Such a method for cutting skin by using cutting means in order to form skin grafts is known from International patent application WO 84/02464. According to FIG. 3 of WO 84/02464 the skin to be cut into skin grafts is placed between a cutting frame and a baseplate, after which the skin is stretched on said baseplate by stretching means fitted with a stretching screw. The cutting operation is carried out by means of a knife which is pulled across the cutting frame. In order to improve the fixation of the skin to be cut pins are provided in the baseplate in regularly spaced-apart relationship, so that the skin cannot move during cutting. In addition to that a cutting foil is present under the skin to be cut, in order to prevent the knives from coming into direct contact with the baseplate. A special drawback of this method is that the pins project into the skin to be cut, which makes it impossible to achieve a 100% yield. In other words, it is not possible to convert 100% of the skin used as the starting material into skin grafts, since a certain amount of skin will be lost as a consequence of being pierced by the pins. Although other methods are mentioned for holding the, skin to be cut in position on the baseplate, for example by using an adhesive, the fixation of the skin to be cut by using a sub-atmospheric pressure or underpressure cannot be derived therefrom.

A method of this kind for forming skin grafts by cutting skin present on a carrier, using cutting means, is already known from the academic dissertation "De techniek van de behandeling van brandwonden" (the technique for treating burns) by R. P. Hermans, published by Stafleu's Wetenschappelijke Uitgeversmaatschappij N. V. of Leiden (see pp. 50–55). According to the said method it is also possible to cover defects caused by burns taking up more than 15–20% of the total surface area of a human body with auto transplants. Split-skin grafts that have been harvested by means of an electro dermatome in a manner which is normal to a person skilled in this field are placed on cork plates which have been immersed in a physiological saline solution. An apparatus known from U.S. Pat. No. 3,076,462, which was specially designed for this purpose, is used to cut said transplants into strips having a width of about 3 mm by means of rotating knives functioning as cutting means, whereby the knives cut through the skin but not through the cork plate, which merely functions as a base. Then the transplant-carrying cork plate is passed through the apparatus anew, but now turned through 90°, so that small squares of about 3×3 mm are formed. The skin grafts thus cut are adhered to gauze, which has been pre-folded in two directions in advance (pleat), by means of a special glue. After the glue has dried the folded gauze is stretched in two directions, as a result of which the skin grafts are spread. This has led to the situation wherein the small squares, viz. the cut skin grafts, are arranged in regularly spaced-apart (about 5 mm) relationship, with the cutting side facing upwards. Then the folded bandage is laid loosely on the excised area, provided with perforations for drainage, and subsequently fixed in position by means of gauze. In this manner an increase in area of about nine times the original dimension is obtained. One drawback of such a method is that after about one week the gauze is removed under an anaesthetic and can be replaced by donor skin. Another drawback is the fact that it takes a considerable amount of routine to be able to carry out such a method. After all, it frequently happens that the skin grafts are detached from the cork plate by the rotating knives and stick to the knives. This problem can be solved, however, by applying a small amount of paraffin to the knives, but this results in insufficient adherence of the skin grafts to the pre-folded gauze. In addition to that it is of paramount importance that the glue be allowed to dry sufficiently long before it is attempted to remove the cork plate from the gauze, as otherwise the skin will not properly adhere to the gauze. Because of the fact that the gauge cannot be removed until after about one week, the healing process, that is, the closing of the wound, will take a period of three to four weeks. In practice such a long healing period is undesirable.

SUMMARY OF THE INVENTION

Now a method for forming skin grafts has been found which does not exhibit the drawbacks of the prior art referred to above. In addition to that the method according to the present invention makes it possible to shorten the healing period by one week, so that the wound will already have closed after a period of two to three weeks.

According to the present invention the method as referred to in the introduction is characterized in that the skin is placed on a porous carrier, whereby a sub-atmospheric or reduced pressure is generated in the holder on the side of the carrier remote from the skin, after which the skin is cut into skin grafts by cutting means.

Although the use of a sub-atmospheric pressure for fixing skin is known from German Gebrauchsmuster No. 94 03 937, it is not known from said document to place the skin on a porous carrier in order to form skin grafts, whereby a sub-atmospheric pressure is generated in the holder, on the side of the carrier remote from the skin, in order to cut the skin thus fixed into skin grafts by cutting means. German Gebrauchsmuster No. 94 03 937 is aimed at the sub-epidermal thinning out of skin for reconstructive purposes, whereas the method according to the present invention comprises a complete cutting through of the skin in order to obtain separate skin grafts.

According to the present invention the term skin is to be understood to mean autologous skin as well as donor skin. In practice it has become apparent, however, that autologous skin "adheres" better than donor skin. In addition to that the term "porous" is understood to mean that a sub-atmospheric pressure can be applied, that is, the carrier is provided with apertures or perforations.

The carrier used according to the present invention is essentially different from the carrier used in U.S. Pat. No. 3,076,462, because the former carrier needs to be porous in connection with the application of a sub-atmospheric pressure, whereas such a requirement is not made of the carrier according to U.S. Pat. No. 3,076,462. Hereafter the term carrier will in all cases be understood to mean a porous carrier.

The carrier used in accordance with the present invention is preferably provided with apertures, in particular conical apertures, whereby the smallest dimension of the cone is located on the side carrying the skin. As a result of the presence of these apertures the generation of a sub-atmospheric pressure in the holder will cause the skin to adhere to the porous carrier, whereby it should be noted that the dimensions of the apertures on the side-carrying the skin are smaller than those of the skin grafts to be cut. If the dimensions of the apertures would exceed those of the skin grafts to be cut, the skin grafts would be sucked out through the apertures of the carrier as a result of the presence of said sub-atmospheric pressure.

In a special embodiment a so-called contra carrier is placed under the apertured or perforated carrier. A contra carrier is a plate provided with protrusions, whereby the diameter of said protrusions is selected to make them fit the apertures of the carrier. The combination of carrier and contra carrier functions to reduce the cross-sectional area of an aperture of the carrier over which the sub-atmospheric pressure is applied. Since a protrusion of the contra carrier projects into an aperture of the carrier, the aperture will be closed to a certain degree. Such a contra carrier is in particular used with thin skin, so that the risk of the cut skin grafts being "sucked out" through the apertures of the carrier is reduced due to the smaller cross-sectional area of the aperture over which the sub-atmospheric pressure is applied. In a preferred embodiment the contra carrier is provided with a plurality of regularly spaced-apart ribs, which ensure that the skin is cut through completely. Preferably the number of protrusions of the contra carrier equals the number of apertures in the carrier. The carrier is preferably made of plastic material, which material is capable of withstanding the force of the knife to be used for cutting. Preferably an elastic plastic material is used, in connection with achieving a proper seal in the recess of the holder.

It is preferred to use a cutting frame for said cutting, which cutting frame is placed on the skin and which is provided with several parallel slots, through which slots a cutting means comprising a knife, preferably a wheel knife, is moved. Such a cutting frame is known per se, in particular from International patent application WO 84/02464. A wheel knife consists of a handle, in one end of which a circular knife is rotatably mounted. By moving the wheel knife through the slots the skin is cut into strips. The skin is first cut in one direction by moving the knife through the parallel slots of the cutting frame. Then the cutting frame is turned through 90° and the skin is cut again in the same manner. In a preferred embodiment of the present invention the skin is turned through 90° with respect to the cutting frame or the cutting means. It has become apparent that turning the skin is easier than turning the cutting frame or the cutting means. The result of such a two-step cutting operation is a carrier on which skin grafts are present. It is also possible, however, to cut the skin present on the carrier without using such a cutting frame, but it is preferred to use a cutting frame in order to obtain uniformly finished skin grafts.

In another embodiment a cutting table provided with cutting knives is used as the cutting means, which cutting table is moved across the skin, whereby the cutting knives are in contact with the skin to be cut. It is also possible, however, to move the skin with respect to the cutting table. The present invention is not limited to any particular movement of the skin to be cut with respect to the cutting table in order to form skin grafts. Preferably such a cutting table comprises regularly spaced-apart cutting knives, which cutting knives are mounted on a common guide rod, as a result of which parallel cuts are obtained in a single operation. In a special embodiment such cutting knives are capable of rotating movement about an axis in the cutting table, thus preventing the skin from being "wound up" and sticking to the cutting knife when the cutting table moves over the skin. The above-described wheel knife is for example a rotary cutting knife, whereby preferably a plurality of such wheel knives are disposed side by side in the cutting table. The use of such cutting means obviates the use of a cutting frame in a great many embodiments, because the knives are fixed in position in the cutting table with respect to the carrier, as a result of which skin grafts of uniform dimensions are obtained in a simple manner.

In the above steps the skin has been cut into skin grafts by the cutting means, that is, the cutting table, which is provided with regularly spaced-apart cutting knives, possibly by using the cutting frame, which is provided with several parallel slots, through which a knife can move. In a special embodiment of the present invention the dimension of the skin grafts is 3×3 mm.

The present invention furthermore relates to a holder to be used in forming skin grafts, which holder Is characterized in that it is provided with a recess, in which the carrier can be placed, possibly in combination with a contra carrier as described before, said holder being provided on the side opposite said recess with a pipe for applying said sub-atmospheric pressure.

According to the present invention the carrier is placed into the recess of tho holder, possibly in combination with a contra carrier, as described before. The (autologous) skin to be cut is placed on the carrier, under which a contra carrier may be present, after which a sub-atmospheric pressure is generated in the holder, on the side of the carrier remote from the skin, by means of a vacuum pump. As a result of this the skin will adhere to the carrier. Then a cutting frame may be placed into the recess of the holder, on the skin adhered to the carrier, and the skin grafts are obtained by means of a knife which is moved across the skin. It is also possible to move the skin with respect to the knife. In another embodiment the holder is placed into a cutting table. Then the skin is cut as described before, after which the skin is turned through 90° and cut again in the same manner in order to obtain skin grafts. It is also possible, of course, to turn the cutting frame or the cutting table through 90° instead of the carrier on which the skin is present and subsequently cut the skin anew.

After the skin grafts have been obtained in accordance with the method according to the present invention, the skin grafts are transferred to the intended place, for example directly to a patient's burn or to spreading means. The transfer of skin grafts is carried out by placing a transport means comprising an apertured side and a connection for applying a sub-atmospheric pressure with the apertured side on the skin or the skin grafts, whereby the skin (grafts) are adhered to the transport means by applying a sub-atmospheric pressure to the transport means, after which the skin (grafts) adhering to the transport means are transported by moving said transport means while maintaining said sub-atmospheric pressure. After the skin or the skin grafts have been transported to the desired place by such transport means, the skin adhering to the transport means is preferably removed therefrom by releasing the sub-atmospheric pressure, as a result of which the force of gravity causes the skin or the skin grafts to become detached from the transport means. Such a transport means is known per se from German Offenlegungsschrift No. 35 37 514 and from International patent application WO 84/02464, which has already been discussed before. In a special embodiment the skin adhering to the transport means is removed therefrom by moving pins from an ejector, which is present in the transport means, through the apertures in the transport means.

The present invention furthermore relates to an ejector to be used in removing the skin adhering to the carrier, which ejector is characterized in that it consists of a supporting plate or central portion provided with pins having a diameter which is smaller than that of the apertures in which the pins are capable of movement. In such an embodiment the ejector is used to detach the skin grafts from the carrier to which they adhere by placing the supporting plate provided with pins under the carrier and subsequently moving the pins through the apertures of the carrier, as a result of which the skin grafts are detached from the carrier. Then the skin grafts thus detached can be transported directly to the burn or to spreading means, using the transport means as already described before, for example, or be placed on the dermis side of the donor skin. To an expert in this field it will be apparent that the skin grafts thus detached can be transported by means of another apparatus suitable for this purpose, for example a pair of tweezers.

The present invention furthermore relates to a method for applying skin grafts to a burn, which method is characterized in that a skin-like material is placed on the skin grafts, after which the skin grafts adhering to said material are applied to the burn. Preferably a gauze of plastic material is used as a suitable skin-like material. More in particular donor skin is used. When the skin grafts are covered with donor skin, the healing process is accelerated, which is desirable in practice.

The present invention will be explained in more detail hereafter by means of the appended examples in conjunction with the illustrated drawings.

DESCRIPTION OF THE DRAWINGS

In the drawings:

FIG. 4b is a side view of the contra carrier shown in FIG. 4a.

FIG. 7b is a front view of the cutting table shown in FIG. 7a.

FIG. 8a shows a separate ejector according to the present invention.

FIG. 8b shows a carrier according to the present invention, which is to be used with the separate ejector according to FIG. 8a.

FIG. 9a shows another embodiment of a separate ejector according to the present invention.

FIG. 9b shows a carrier according to the present invention to be used with the separate ejector according to FIG. 9a.

DETAILED DESCRIPTION

Figure 1A:
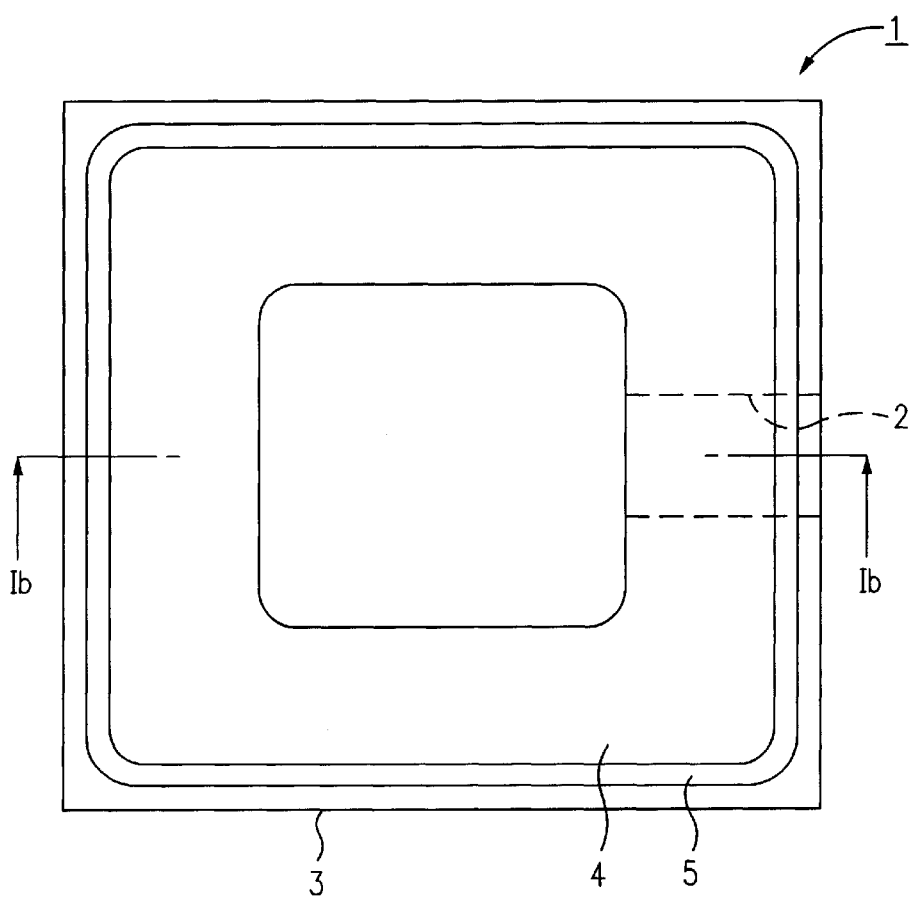
FIG. 1a is a plan view of a holder for forming skin grafts according to the present invention.
Figure 1B:
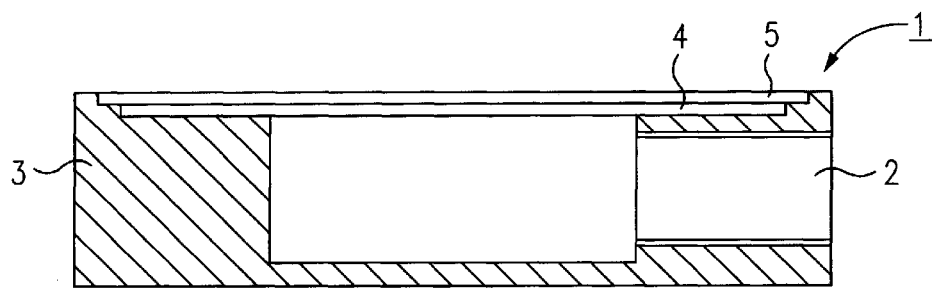
FIG. 1b is a cross-sectional view of the holder shown in FIG. 1a, along line Ib—Ib.

The holder 3 shown in FIGS. 1a, 1b comprises a connection 2 for sub-atmospheric pressure. Holder 3 is provided with a recess 4, in which a carrier (not shown) can be placed. After a carrier, which may be provided with a contra carrier (not shown), has been placed into recess 4, a cutting frame (not shown) is placed into recess 5. A sub-atmospheric pressure is generated in the interior of holder 3 by connecting connection 2 for sub-atmospheric pressure to a vacuum pump (not shown). The holder may comprise compressing means (not shown) in order to effect a proper sealing in the holder of the carrier, which may be provided with a contra carrier and a cutting frame.

Figure 2:
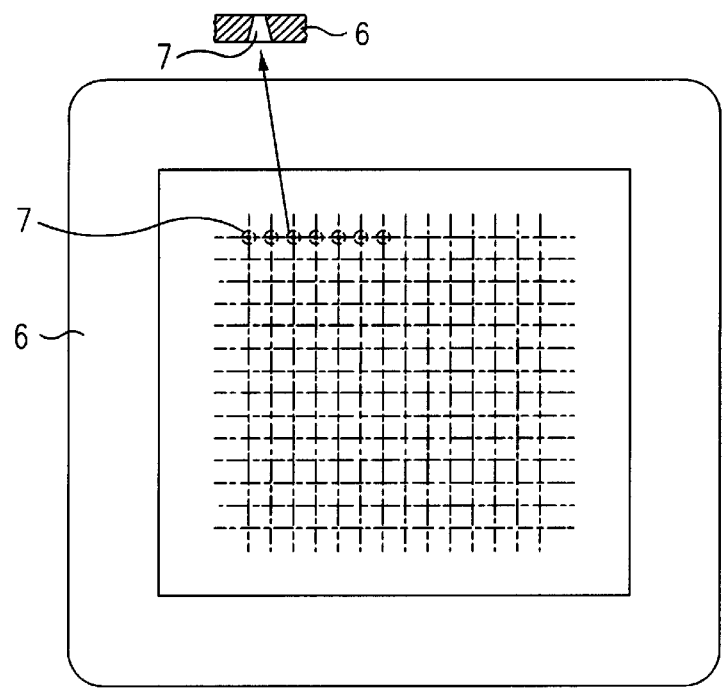
FIG. 2 shows an apertured carrier according to the present invention.

The carrier 6 shown in FIG. 2 comprises a plurality of regularly spaced-apart apertures 7. Such apertures 7 are preferably conical, whereby the smallest dimension of the aperture is located at the surface of carrier 6.

Figure 3:
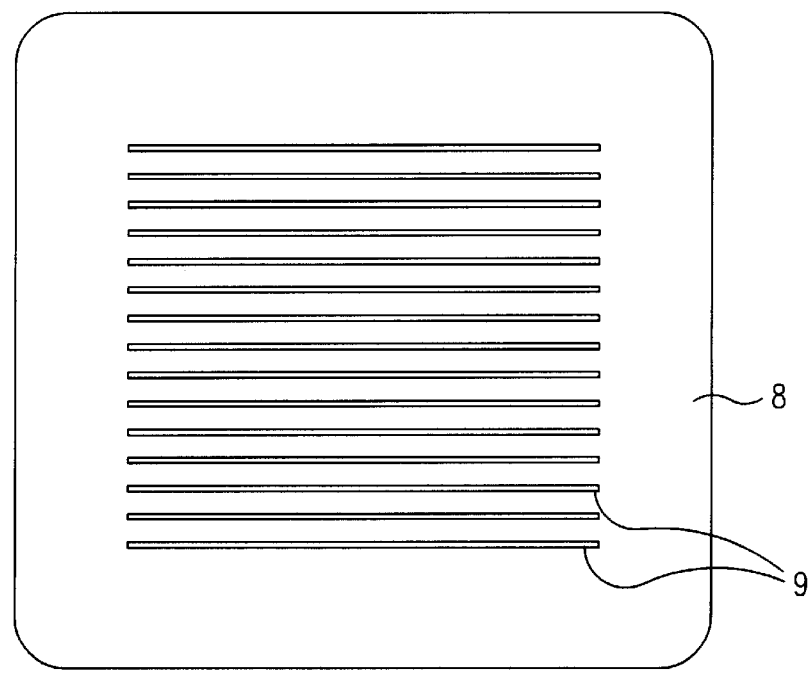
FIG. 3 shows a cutting frame to be used with the holder shown in FIG. 1.

Cutting frame 8 in FIG. 3 comprises a plurality of parallel slots 9, through which a knife (not shown) is capable of movement.

Figure 4A:
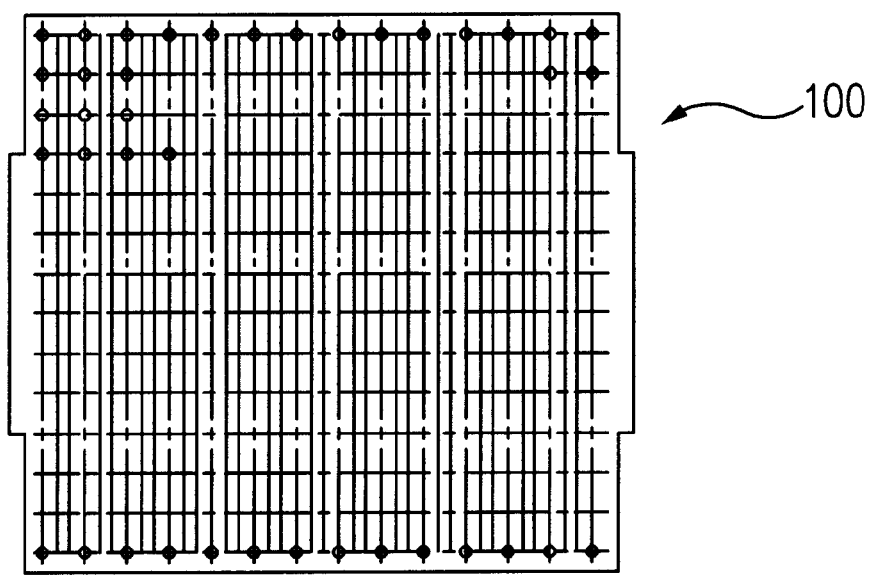
FIG. 4a is a plan view of a contra carrier to be used in forming skin grafts according to the present invention.

FIG. 4a shows a contra carrier 100 provided with protrusions 101.

Figure 4B:
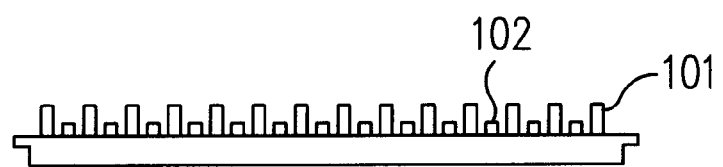

FIG. 4b shows the contra carrier 100 shown in FIG. 4a, wherein a number of ribs 102 are present between protrusions 101 in order to obtain a complete cutting of the skin.

The method for forming skin grafts is carried out by placing skin from a patient on carrier 6, whereby the total area of the skin equals the total area of the part of carrier 6 that is provided with apertures 7. If the total area of the skin is smaller than the total area of a carrier 6 that is provided with apertures 71 the skin will not sufficiently adhere to carrier 6, because of the absence of a vacuum, which is caused by the fact that air is sucked in through the apertures 7 of carrier 6 not covered by skin. Subsequently carrier 6, on which skin is present, is placed into recess 4 of holder 3.

Possibly a contra carrier 100 provided with protrusions 101 can be placed under carrier 6, whereby said protrusions project into apertures 7 of carrier 6, as a result of which the cross-sectional area of apertures 7 is reduced. Then a sub-atmospheric pressure is applied to holder 3 by connecting connection 2 for sub-atmospheric pressure to a vacuum pump, as a result of which the skin present on carrier 6 is firmly adhered to said carrier 6. After the skin has been firmly adhered to carrier 6, cutting frame 8 may be placed into recess 5 of holder 3. The whole may be pressed down by hand. A cutting knife, possibly a wheel knife, is moved through parallel slots 9 of cutting frame 8, maintaining the sub-atmospheric pressure being applied to holder 3, as a result of which the skin present on carrier 6 is cut into parallel strips. In order to obtain square skin grafts, cutting frame 8 is then removed from recess 5 of holder 3 whilst maintaining the sub-atmospheric pressure, and subsequently replaced therein, albeit in a position turned through 90°. Square skin grafts are obtained by moving a knife through parallel slots 9 again. The skin grafts thus obtained on carrier 6 can be removed from holder 3 by first removing cutting frame 8 from recess 5 of holder 3. It is also possible, however, to cut the skin adhering to the carrier without using a cutting frame.

Figure 5:
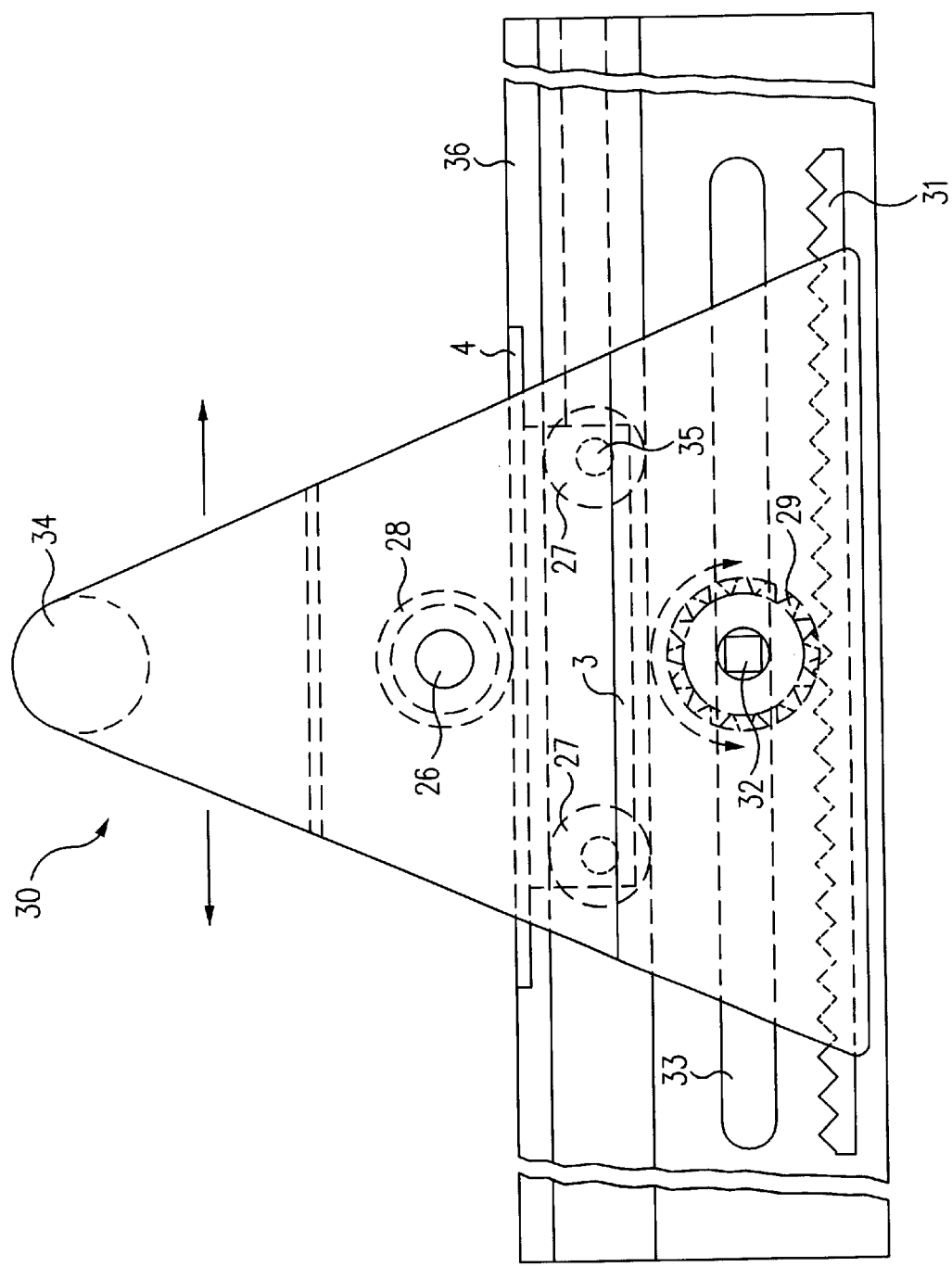
FIG. 5 is a side view of a cutting table to be used in forming skin grafts according to the present invention.

FIG. 5 shows a side view of cutting table 30, wherein holder 3 comprising recess 4, in which a carrier (not shown) can be placed, is disposed at a fixed location in support 36 of cutting table 30. One or more cutting knives 28 are rotatably mounted on guide rod 26, which cutting knives 28 are in contact with the skin of carrier 6 (not shown) present in recess 4. Guide rod 26 is mounted in support 34, which support 34 is connected to a transport wheel 29 mounted on pin 32. Transport wheel 29 is capable of movement over transport rail 31 within transport space 33, whereby transport wheel 29 engages transport rail 31. Holder 3 can be placed into support 36, which support 36 is connected to guide wheel 27, which is connected to support 34 via guide pin 35.

Figure 6:
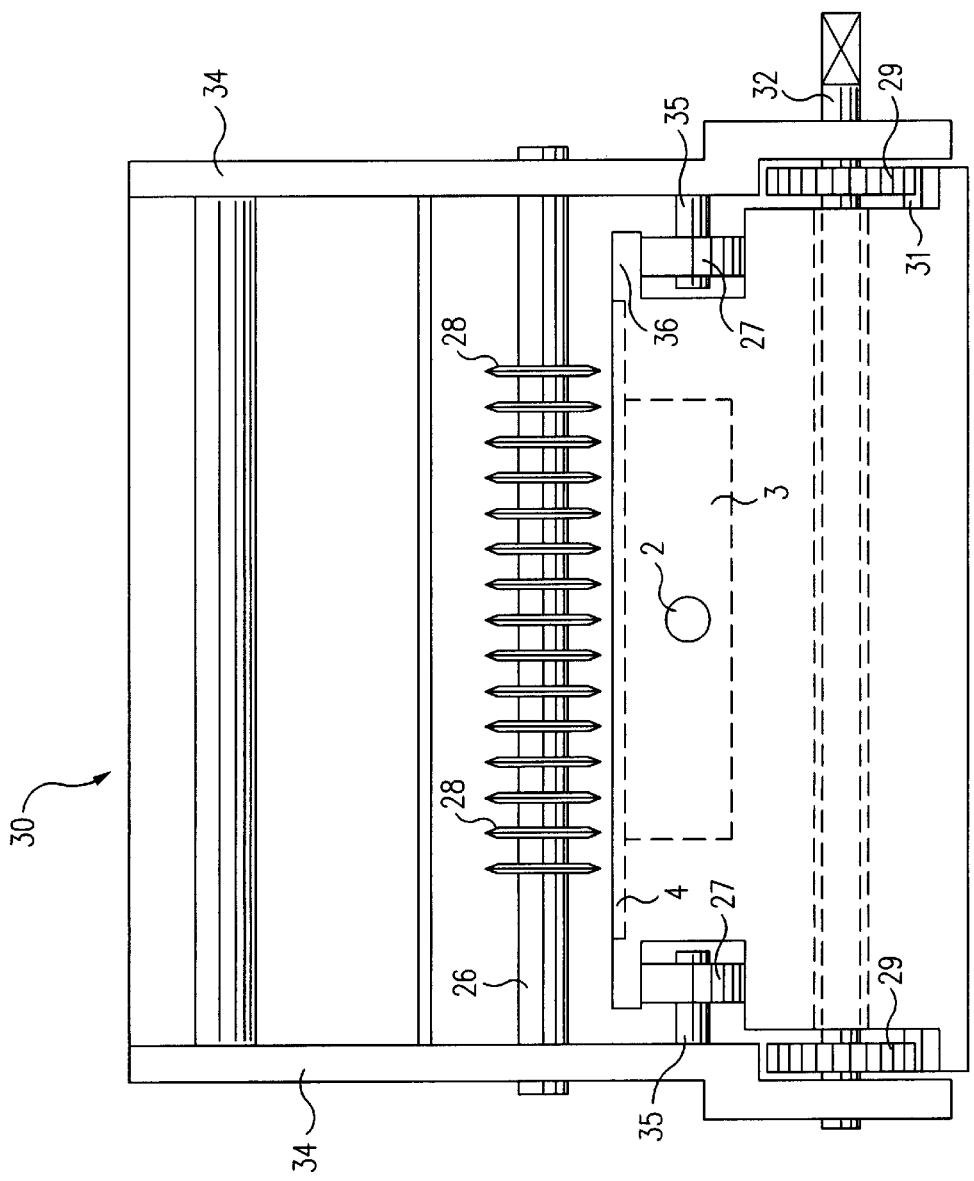
FIG. 6 is a front view of the cutting table of FIG. 5.

FIG. 6 shows a front view of cutting table 30.

Now the method for forming skin grafts by means of the above-described holder 3 and cutting table 30 will be described in more detail. Carrier 6, on which skin is present, is placed into recess 4 of holder 3. A contra carrier 100 may be provided under carrier 6 as described above. Then a sub-atmospheric pressure is applied to holder 3 by connecting connection 2 for sub-atmospheric pressure to a vacuum pump (not shown), as a result of which the skin present on carrier 6 is firmly adhered to said carrier. Then holder 3 is placed into support 36 of cutting table 30. The skin adhered to carrier 6 is cut by bringing the cutting knives 28 present on guide rod 26 in contact with the skin and subsequently moving cutting knives 28 in the direction indicated by the arrows by moving transport wheel 29 in transport space 33. Guide pin 35 and guide wheel 27 connected to support 34, which are furthermore connected to support 36 accommodating holder 3, ensure that the knives 28 are in contact with the skin to be cut, which is present on carrier 6. Cutting knives 28 are moved in the direction indicated by arrows over the distance bounded by transport space 33, maintaining the sub-atmospheric pressure on holder 3, as a result of which the skin present on carrier 6 is cut into parallel strips. Then, in order to obtain square skin grafts; the carrier 6 present in recess 4 is turned through 90° and subsequently replaced into recess 4. The square skin grafts are obtained by moving cutting knives 28 in the above-described manner again. After the square skin grafts have been obtained, holder 3 is removed from cutting table 30. The advantage of the cutting of skin grafts by means of cutting table 30 is that skin grafts are obtained in two cutting movements as a result of the presence of the number of knives 28 mounted on guide rod 26, as a result of which the time required for obtaining skin grafts has been considerably reduced.

Figure 7A:
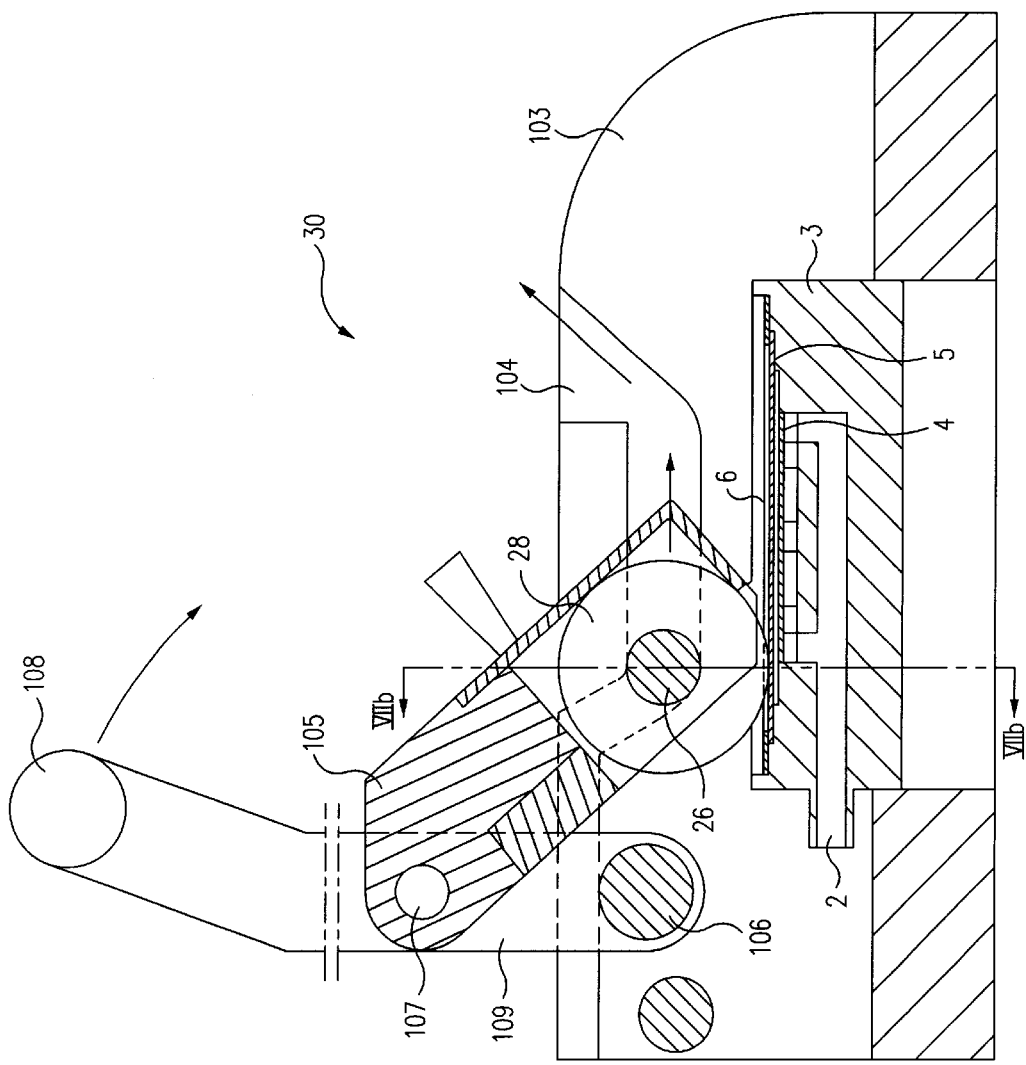
FIG. 7a is a side view of a special embodiment of a cutting table, which is to be used in forming skin grafts according to the present invention.

Now FIGS. 7a and 7b will be described. FIG. 7a is a side view of a special embodiment of a cutting table 30. Cutting table 30 comprises a support 103, into which holder 3 can be placed. The holder 3 used in FIG. 7a corresponds with the holder 3 shown in FIGS. 1a and 1b. Support 103 is provided on both long sides with a guide rail 104, into which the ends of guide rod 26 engage. Guide rod 26 is provided with regularly spaced-apart cutting knives 28, which cutting knives 28 may be brought into contact with the skin adhering to carrier 6 by moving cutting knives 28 in the direction indicated by the arrows by moving guide rod 26 through guide rail 104. Guide rod 26 is furthermore connected to intermediate part 105, which is connected, via hinge point 107, to arm 109 connected to handle 108. Arm 109 is in contact with support 103 via connecting point 106. Moving handle 108 in the direction indicated by the arrow will produce a force resulting from the pivoting movement about connecting point 106, which force is transmitted to intermediate part 105 via hinge point 107, as a result of which cutting knives 28 are brought into contact-with the skin adhering to carrier 6. Cutting knives 28 are moved through guide rail 104 in the direction indicated by the arrows, and thus the skin adhering to carrier 6 is cut in one operation. The result of such an operation is that the skin adhering to carrier 6 is cut into parallel strips. The above-described cutting operation is repeated in order to obtain square skin grafts by removing the skin adhering to carrier 6, turning it through 90°, and subsequently replace it into holder 3.

Figure 7B:
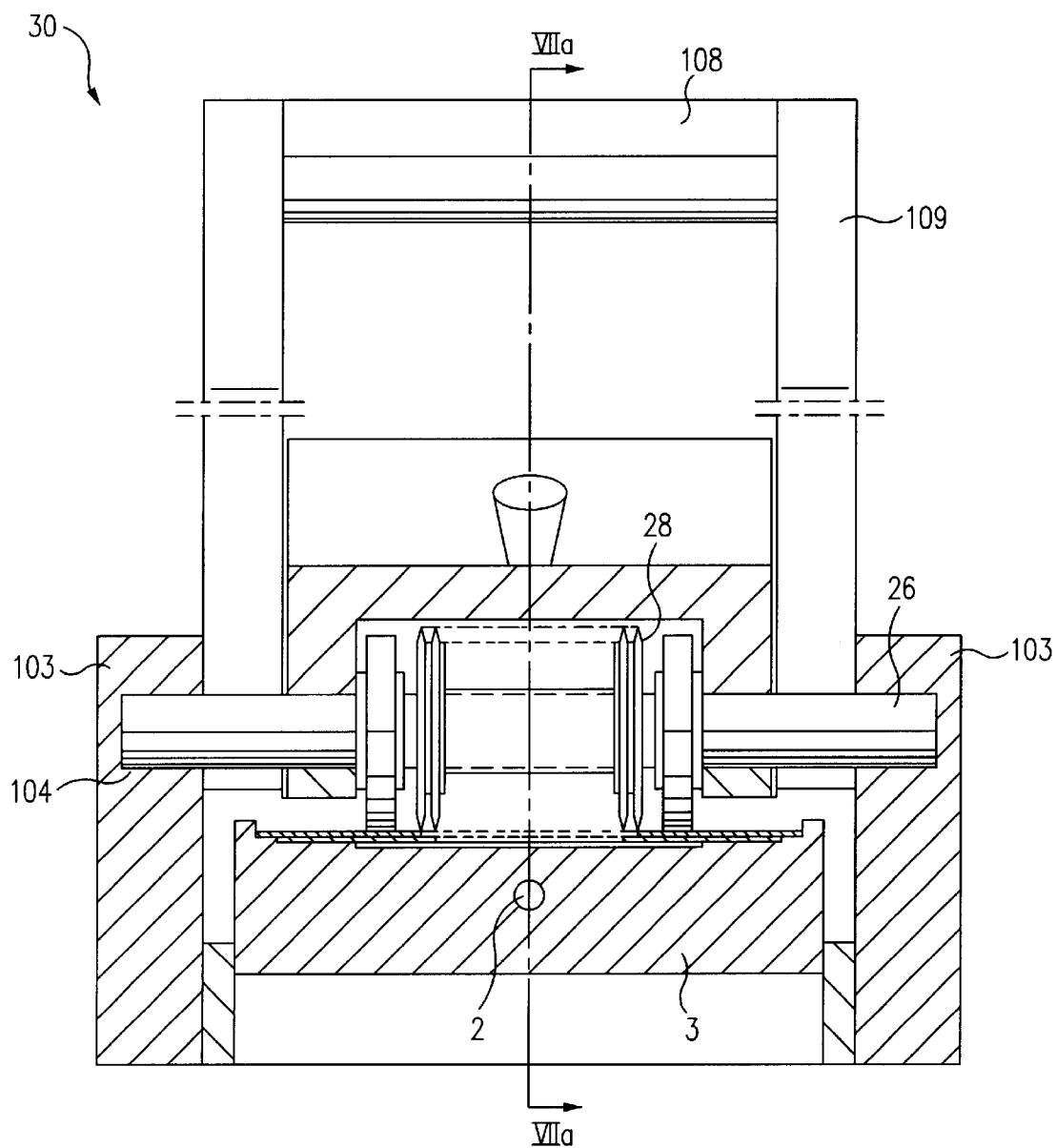

FIG. 7b is a front view of the cutting table 30 shown in FIG. 7a. FIG. 7b shows clearly that cutting knives 28 are present on guide rod 26 In regularly spaced-apart relationship, which cutting knives may be brought into contact with the skin adhering to carrier 6. The cutting of the skin adhering to carrier 6 may be carried out by using the cutting frame 8 shown in FIG. 3. Cutting framer 8 is placed into holder 3 to that end, and the cutting operation as described before will be carried out. Care must be taken, however, that the cutting knives are moved through slots 9 of cutting frame 8, so that incomplete cutting of the skin is prevented.

In a special embodiment a transport means is then placed on the skin thus cut. A suitable transport means is the transport means described in German Offenlegungsschrift No. 35 37 514 and in International patent application WO 84/02464. The transport means is moved to the desired position while maintaining a sub-atmospheric pressure.

Figure 10:
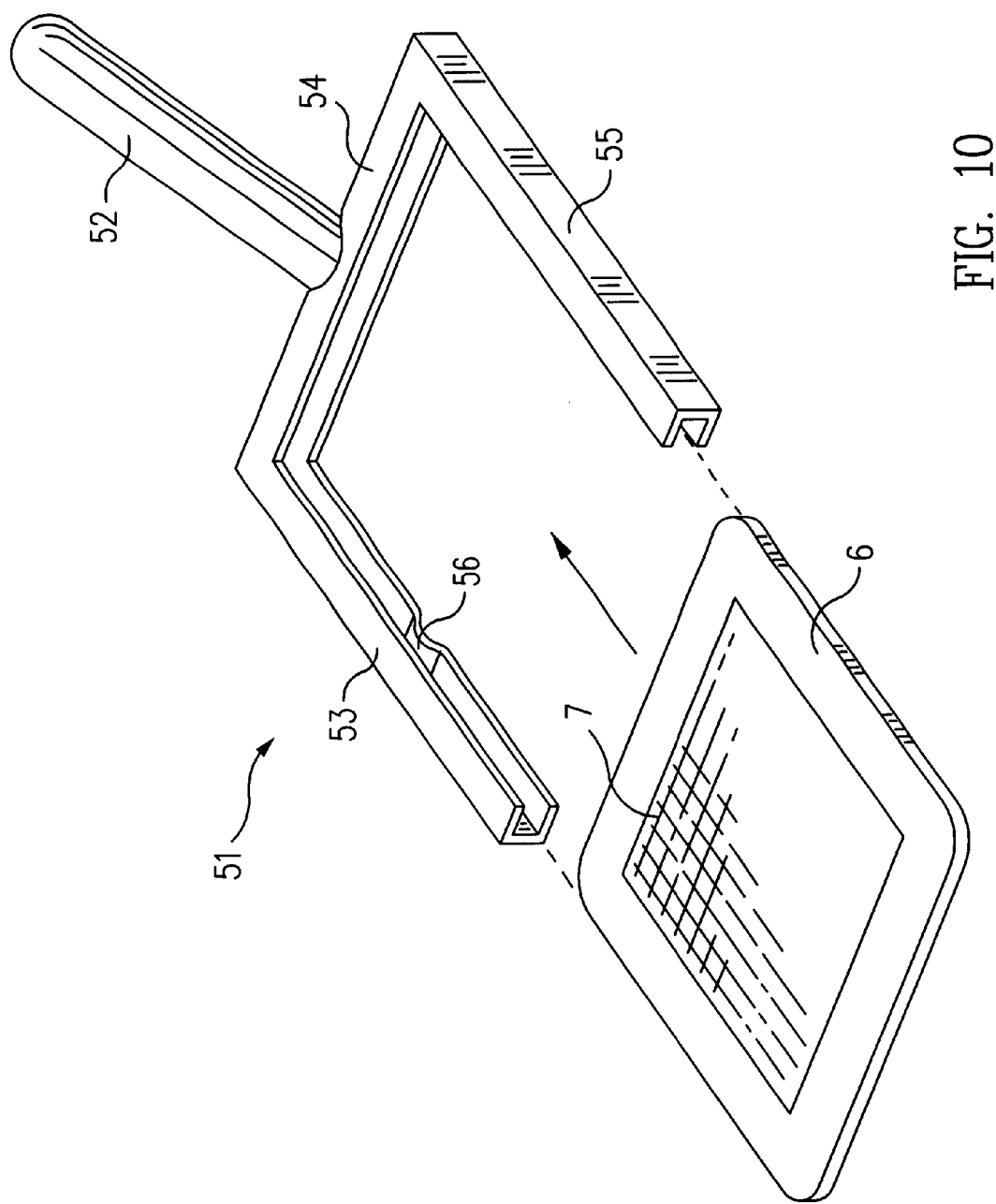
FIG. 10 shows a clamping member to be used in accordance with the present invention, in which a carrier can be clamped down.

As described above, the skin grafts that have been cut on carrier 6 can be transported by using the transport means. It is also possible, however, to transport the skin grafts that have been cut on carrier 6 by using clamping means 51 shown in FIG. 10. According to FIG. 10 clamping means 51 comprises a handle 52, which is connected to side 54, which side 54 is connected on-respective ends to sides 53, 55. Carrier 6, on which cut skin is present, can be clamped down in clamping means 51 by transporting carrier 6 in the direction indicated by the arrow in FIG. 10. In order to prevent carrier 6, which is clamped down between sides 53, 54 and 55, sliding out of clamping means 51, it is preferred to provide elevation 56 in at least one side. Elevation 56 is in particular present in sides 53 and 55. Once carrier 6 has been clamped down in clamping means 51, the whole can be transported by means of handle 52 to donor skin, for example, or directly to a burn. In order to remove the skin adhered to carrier 6 a separate ejector is preferably used, as is indicated by numerals 49 and 50 in FIGS. 8A and 9A respectively. The separate ejectors 49, 50 shown in FIGS. 8A and 9A respectively comprise a handle 48 and a central portion 47 connected thereto, which central portion 47 is provided with pins 46. The skin present on carrier 6 can be removed therefrom by moving pins 46 of separate ejector 49, 50 through the apertures 7 in carrier 6. In one embodiment the number of pins 46 equals the number of apertures 7 in carrier 6, as is shown in FIGS. 8A and 8B. In another embodiment the number of pins 46 is lower than the number of apertures 7 in carrier 6, as is shown in FIGS. 9A and 9B. The advantage of the separate ejector 50 shown in FIG. 9A is that only a certain number of skin grafts are detached from carrier 6. According to this embodiment a desired number of skin grafts can be detached from carrier 6, using a desired in-between distance, as a result of which a certain spreading of skin grafts is achieved already. In certain embodiments the skin grafts that have been detached by means of ejector 50 can be transferred directly to for example a burn, therefore. It will be apparent that the present invention is not limited to the geometry of the pins 46 that is shown in FIGS. 8A and 9A.

Based on their experience and insight those skilled in this field are convinced that if skin grafts obtained by using the method according to the present invention are used, which are subsequently applied to a burn, the healing process of a burn can be shortened by one week in comparison with the healing process according to the currently used methods.

What is claimed is:

1. A method for forming skin grafts by cutting skin present on a porous carrier, using cutting means, whereby the carrier has a first side on which skin can be placed and a second side remote from the skin and is present in a holder, characterized placing skin on said first side of said porous carrier;

generating a sub-atmospheric pressure in the holder on the second side of the carrier remote from the skin; and cutting the skin into skin grafts.

2. A method according to claim 1, further characterized in that apertures in said porous carrier are formed by a process including the step of:

forming conical apertures from the second side to the first side of said carrier.

3. A method according to claim 2, further characterized in that said step of forming conical apertures comprises:

forming conical apertures from the second side to the first side of said carrier, whereby the smallest dimension of each cone is located on the first side of the carrier carrying the skin.

4. A method according to claim 2 further characterized in that the dimensions of the apertures in contact with the skin are smaller than those of the skin, grafts to be cut.

5. A method according to claim 1, further characterized in that said carrier is made of plastic material.

6. A method according to claim 1, further characterized by:

placing a contra carrier with protrusions on the second side of the carrier such that said protrusions extend into said apertures of the carrier thereby to reduce the cross sectional area of said apertures through which air can flow;

placing the assembly consisting of the skin, the carrier and the contra carrier into the holder;

generating a sub-atmospheric pressure in said holder so as to hold the skin against the first side of the carrier; and cutting the skin.

7. A method according to claim 1, characterized by cutting the skin using a cutting frame, which cutting frame is placed on the skin and which is provided with several parallel slots, through which slots one or more knives are moved to cut the skin.

8. A method according to claim 1, characterized by:

using a cutting table as the cutting means by:

moving the cutting table over the skin adhering to the first side of the carrier,; and providing several regularly spaced-apart cutting knives in contact with the skin to be cut so as to cut the skin as the cutting table is moved over the skin.

9. A method according to claim 1, characterized in that said carrier is porous by providing said carrier with conical apertures.

10. A method according to claim 9, characterized by providing said carrier with conically shaped apertures wherein the smallest dimension of each aperture is at the first side.

11. A method according to claim 9, characterized by making said carrier of plastic material.

12. A method for applying skin grafts to a burn, characterized by placing a skin-like material on skin grafts obtained in accordance with the method of claim 1, and then applying the skin grafts adhering to said material to the burn.

13. A method according to claim 12, characterized by using a gauze of plastic material as said skin-like material.

14. A method according to claim 12, characterized by using donor skin as said skin-like material.

* * * * *